United States Patent [19]

Edwards

[11] Patent Number: 4,888,327
[45] Date of Patent: Dec. 19, 1989

[54] TOPICAL ANTIBIOTIC COMPOSITIONS

[75] Inventor: John G. Edwards, Cleburne, Tex.

[73] Assignee: Alcon Laboratories, Inc., Fort Worth, Tex.

[21] Appl. No.: 228,621

[22] Filed: Aug. 4, 1988

Related U.S. Application Data

[63] Continuation of Ser. No. 18,330, Feb. 24, 1987, abandoned, which is a continuation of Ser. No. 659,352, Oct. 10, 1984, abandoned.

[51] Int. Cl.$^4$ .................. A61K 31/70; A61K 31/635; A61K 31/505
[52] U.S. Cl. ........................................ 514/41; 514/40; 514/158; 514/272
[58] Field of Search .................... 514/40, 41, 158, 272

[56] References Cited

PUBLICATIONS

Bodey et al., Review of Infectious Diseases, vol. 4, No. 2, 1982, pp. 579–585.
Grose et al., Am. Jour. Med. Sci., vol. 279, No. 1 (1980), pp. 4–13.
PDR, 35 Ed., 1981, p. 765.

*Primary Examiner*—Jerome D. Goldberg
*Attorney, Agent, or Firm*—James A. Arno; Gregg C. Brown

[57] ABSTRACT

Disclosed are antibiotic compositions for topical administration comprising an aminoglycoside, a benzylpyrimidine and a sulfonamide.

2 Claims, No Drawings

TOPICAL ANTIBIOTIC COMPOSITIONS

Continuation of Ser. No. 018,330, filed Feb. 24, 1987, now abandoned, which is a continuation of Ser. No. 659,352, filed Oct. 10, 1984, now abandoned.

BACKGROUND OF THE INVENTION

1. Field of the Invention

This invention relates to antibiotic combinations for topical use. Specifically, it relates to the synergistic combination of an aminoglycoside, a benzylpyrimidine, and a sulfonamide.

2. Description of the Prior Art

Aminoglycosides are antibiotics which inhibit bacterial protein syntheses. Sulfonamides competively inhibit the utilization of paraamino-benzoic acid by bacteria which synthesize folic acid. Benzylpyrimidine like trimethoprim, also interfere in the synthesis bacterial folic acid at a stage just following the supposed interference by the sulfonamide. The advantages of the sequential involvement of sulfonamides and benzylpyrimidines in the interference of folic acid synthesis, purines and, ultimately, bacterial DNA have been exploited by their synergistic combination. Such combinations (e.g., co-trimoxazole =trimethoprim and sulfamethoxazole) are particularly useful in treating urinary tract infections. Combinations of trimethoprim and polypeptide antibiotics, such as polymyxin, or aminoglycosides, such as gentamicin, have been shown to be synergistic in vitro (*Proc 10th Intl Congress Chemother.* 438–439 [1978]). The combination of tobramycin with trimethoprim and sulfamethoxazole is also known an synergy has been alleged; however, such prior art combinations were limited to clinical evaluation of cancer patients' response on the separate intravenous administration of tobramycin and trimethoprim-sulfamethoxazole dosage (oral or intravenous) regimens (*Rev. Inf. Disease* 4 [4]:579–585 [1982]; Am. *J. Med. Sci.* 279 [1]:4–13 [1980]). Some in vitro synergy against *Serratia marcescens* was demonstrated between co-trimoxazole and gentamicin (*Proc 10th Intl Congress Chemother.* 434–436[1978]). Beyond these experiences, there is nothing in the prior art which would suggest the topical combinations of the present invention or their precise concentration ranges which achieve true synergy of all components without creating or enhancing any antagonistic effects of any pair.

SUMMARY OF THE INVENTION

The present invention is directed toward providing topical antibiotic compositions which are useful in the treatment of ocular, otic and dermal infections. The compositions of the present invention include, as a principal active ingredient, a synergistic combination of an aminoglycoside, a benzylpyrimidine and a sulfonamide. These compositions have been found to be especially useful in treating infected ocular tissues.

Thus it is an object of the present invention to provide a topical antibiotic combination comprising an aminoglycoside, a benzylpyrimidine, and a sulfonamide in formulations which are synergistic, that is, demonstrate increased efficacy, spectrum, and safety. It is a further object of the present invention to provide a combination of an aminoglycoside, a benzylpyrimidine and a sulfonamide which is useful in treating ocular, otic or dermal infections.

DESCRIPTION OF THE PREFERRED EMBODIMENTS

The compositions of the present invention comprise a synergistic combination of an aminoglycoside component, a benzylpyrimidine component and a sulfonamide component; wherein each component is recited in the generic sense, it being understood that the nomenclature utilized herein is embracive of all known salts and analogues of such compounds. The preferred ratio of aminoglycoside component: benzylpyrimidine component: sulfonamide component in this synergistic combination is as follows:

|  | Range, Weight Ratio |
|---|---|
| aminoglycoside | 0.1 to 1.0 |
| benzylpyrimidine | 1 to 10.0 |
| sulfonamide | 2 to 20.0 |

Examples of aminoglycosides which may be utilized in the synergistic combinations of the present invention include:
5-episisomicin,
amikacin,
butirosin,
BB-K122,
diberkacin,
fortimicin A,
gentamicin,
kanamycin,
kanendomycin,
neomycin,
netilmycin,
sagamicin,
sisomicin,
streptomycin, and
tobramycin.

The foregoing aminoglycosides are given by way of illustration, not limitation.

Examples of benzylpyrimidines which may be utilized in the synergistic combinations of the present invention include:
brodimoprim (RO 10-5970),
metioprim (RO 12-6995),
RO 11-8958,
tetroxoprim, and
trimethoprim.

The foregoing benzylpyrimidines are given by way of illustration, not limitation.

Examples of sulfonamides which may be utilized in the synergistic combinations of the present invention include:
4-homosulfanilamide,
4-homosulfanilamide propionate,
N-Acetylsulfanilamide,
p-aminoethylbenzene sulfonamide,
sodium sulfacetamide,
sodium sulfadiazine,
sodium sulfaethidole,
sulfadimethoxine,
sulfadoxine,
sulfamethazine,
sulfamethizole,
sulfamethoxazole,
sulfamethoxy pyridazine,
sulfamoxole, sulfisomidine,
sulfisoxazole, and
sulfisoxazole diolamine.

The foregoing sulfonamides are given by way of illustration, not limitation.

While all permutations of the above components are preferred expressions of the present invention, the following combinations with tobramycin are especially preferred:

| | |
|---|---|
| tobramycin | 0.01% |
| trimethoprim | 0.1% |
| sulfamethoxazole | 0.2% |
| tobramycin | 0.01% |
| metioprim | 0.1% |
| sulfamethoxypyridazine | 0.2% |
| tobramycin | 0.03% |
| brodimoprim | 0.3% |
| sodium sulfacetamide | 1.5% |
| tobramycin | 0.05% |
| trimethoprim | 0.5% |
| sulfadimethoxine | 2.5% |
| tobramycin | 0.01% |
| trimethoprim | 2.0% |
| sulfisoxazole diolamine | 4.0% |

With respect to the preferred indication for ocular infections, the combinations of the present invention are formulated as aqueous solutions, suspensions, ointments or gels. The recommended dosage regimen is left to the routine discretion of the clinician, but, as a general guide, one or two drops are applied to the afflicted eye one to four times daily. Gelled compositions are delivered at comparable dosage levels.

The compositions of the present invention are particularly effective against the following organisms:

| Gram-positive Bacteria | Gram-negative Bacteria |
|---|---|
| *Staphylococcus aureus* | *Klebsiella pneumoniae* |
| *Staphylococcus epidermidis* | *Escherichia coli* |
| *Streptococcus pneumoniae* | *Proteus* sp. |
| *Streptococcus pyogenes* | *Moraxella* sp. |
| *Streptococcus* (viridans group) | *Haemophilus* sp. |
| Group B. *Streptococcus* | *Neisseria* sp. |
| *Micrococcus* sp. | *Serratia marcescens* |
| | *Acinetobacter calcoaceticus* |
| | *Pseudomona aeruginosa* |
| | *Escherichia coli* |
| | *Enterobacter aerogenes* |
| | *Chlamydia trachomatis* |

The following examples illustrate, but do not limit the compositions of the present invention.

EXAMPLE 1

Aqueous solutions and Suspensions

Effective ophthalmic solutions and suspensions, which include a synergistic combination of an aminoglycoside, a benzylpyrimidine and a sulfonamide as a principal active ingredient, may be prepared using a formulation similar or identical to the one listed for illustration below:

| Example of Ophthalmic Solution Formulation | |
|---|---|
| Ingredient | Amount |
| Tobramycin | 0.1 mg/mL (0.01 wt %) |
| Benzylpyrimidine | 1 mg/mL (0.1 wt %) |
| Sulfisoxazole | 2 mg/mL (0.2 wt %) |
| Boric Acid | 12.4 mg/mL (1.25 wt %) |
| Sodium Sulfate | 12 mg/ml (1.2 wt %) |
| Sodium Chloride | 3.0 mg/mL (0.3 wt %) |
| Benzalkonium Chloride | 0.1 mg/mL (0.01 wt %) |
| Tyloxapol | 0.5 mg/mL (0.05 wt %) |
| Sodium Hydroxide and/or Sulfuric Acid | qs to adjust pH to 5–8 |
| Purified Water | qs to adjust volume |

The above formulation may be prepared, for example, as follows. First, trimethoprim and subsequently sulfisoxazole are dissolved in purified water under stirring and heating in a water bath. The tobramycin is then added, followed by addition of the boric acid, sodium sulfate, sodium chloride and tyloxapol. The solution is then made up to final volume with purified water after adjusting the pH to 5.0–8.0 with sodium hydroxide and/or sulfuric acid.

EXAMPLE 2

Gel System

Effective ophthalmic gels, which include a synergistic combination of an aminoglycoside, a benzylpyrimidine and a sulfonamide as a principal active ingredient, may be prepared using gel vehicles, such as carboxypolymethylene, a carboxy vinyl polymer (available under the trade name Carbopol from the B.F. Goodrich Company); or ethylene maleic anhydride (available under the trade name EMA from the Monsanto Company), in combination with an appropriate preservative, i.e., trimerosal, benzalkonium chloride, 1-methyl and/or propylparaben, or chlorobutanol.

The gel polymer is dispersed in water, then a basic (nondrug) agent is added, such as ammonium hydroxide, sodium hydroxide, ethanolamine or other basic compounds to provide a desired pH of from 4.5 to about 6.5. After the gel has been formed in this manner, the drugs and preservative are added.

An example of a suitable ophthalmic gel formulation for this invention is listed for illustration below:

| Example of Ophthalmic Gel Formulation | |
|---|---|
| Ingredient | Amount |
| Tobramycin | 3 mg/g (0.3 wt %) |
| Trimethoprim | 3 mg/g (0.3 wt %) |
| Sulfonamide | 60 mg/g (6.0 wt %) |
| Carbopol | 50 mg/g (5.0 wt %) |
| Chlorobutanol | 5 mg/g (0.5 wt %) |

This example is given by way of illustration and not limitation.

EXAMPLE 3

Ophthalmic Ointment

Effective ophthalmic ointments, which include a synergistic combination of an aminoglycoside, a benzylpyrimidine and a sulfonamide as a principal active ingredient, may be prepared using ointment vehicles such as white petrolatum, liquid petrolatum, liquid lanolin, glycerin and/or mineral oil in combination with appropriate preservatives (see Example 2 for a list of preservatives). These ointment vehicles serve as illustrations, not limitations to a pharmaceutically acceptable ointment carrier.

An example of a suitable ophthalmic ointment formulation for this invention is listed for illustration below:

| Example of Ophthalmic Ointment Formulation | |
| --- | --- |
| Ingredient | Amount |
| Tobramycin | 3 mg/g (0.3 wt %) |
| Trimethoprim | 3 mg/g (0.3 wt %) |
| Sulfonamide | 60 mg/g (6.0 wt %) |
| Mineral Oil | 150 mg/g (15.0 wt %) |
| Petrolatum Base | 200 mg/g (20.0 wt %) |
| Chlorobutanol | 5 mg/g (0.5 wt %) |

This example is given by way of illustration and not limitation.

In this disclosure, there is described only the preferred embodiments of the invention. It is to be understood that the invention is capable of changes or modifications within the scope of the invention concept defined by the claims which follow.

I claim:

1. A method of treating ophthalmic bacterial infections in humans which comprises applying topically to an infected eye a therapeutically effective amount of an ophthalmic composition comprising tobramycin, trimethoprim and sulfamethoxazole, wherein the weight ratio of tobramycin trimethoprim and sulfamethoxazole is in the range of 0.1 to 10: 1 to 10: 2 to 20.

2. A method according to claim 1 wherein the composition includes 0.01 wt. % tobramycin, 0.1 wt. % trimethoprim and 0.2 wt. % sulfamethoxazole.

* * * * *